(12) United States Patent
Arnissolle

(10) Patent No.: US 6,511,460 B1
(45) Date of Patent: Jan. 28, 2003

(54) INJECTION SYRINGE WITH EXTERNALLY MOBILE NEEDLE SHIELD

(75) Inventor: Yves Arnissolle, Saint Genis Laval (FR)

(73) Assignee: Sedat, Irigny (FR)

(*) Notice: Subject to any disclaimer, the term of this patent is extended or adjusted under 35 U.S.C. 154(b) by 0 days.

(21) Appl. No.: 09/762,266
(22) PCT Filed: Jul. 20, 1999
(86) PCT No.: PCT/FR99/01775
§ 371 (c)(1), (2), (4) Date: Jul. 10, 2001
(87) PCT Pub. No.: WO00/07649
PCT Pub. Date: Feb. 17, 2000

(30) Foreign Application Priority Data

Aug. 7, 1998 (FR) .............................. 98/10218

(51) Int. Cl.[7] .............................. A61M 5/32; A61M 5/00
(52) U.S. Cl. ........................................ 604/197; 604/110
(58) Field of Search ................................ 604/192, 197, 604/198, 110, 263, 227, 164.08; 128/919

(56) References Cited

U.S. PATENT DOCUMENTS 5,713,871 A * 2/1998 Stock .......................... 604/192

FOREIGN PATENT DOCUMENTS

FR 2770405 * 10/1997

* cited by examiner

Primary Examiner—Brian L. Casler
Assistant Examiner—Catherine Serke
(74) Attorney, Agent, or Firm—Sughrue Mion, PLLC

(57) ABSTRACT

An injection syringe (10) has an elongated syringe body (12) including a tube (18), a perforated front wall (26) for receiving an injection needle (70), and a rear actuating plunger (14) movably mounted inside the tube (18). A mobile needle shield (16) is externally movable along the syringe body (12) between a retracted position and an active position. An axial coupling mechanism (54) is provided between the shield (16) and the actuating plunger (14) for their simultaneous displacement towards the front on a common section. A release mechanism (58) is provided for releasing the coupling mechanism (54) to disengage the actuating plunger (14) and the needle shield (16) when the needle shield (16) is finally set in place.

8 Claims, 2 Drawing Sheets

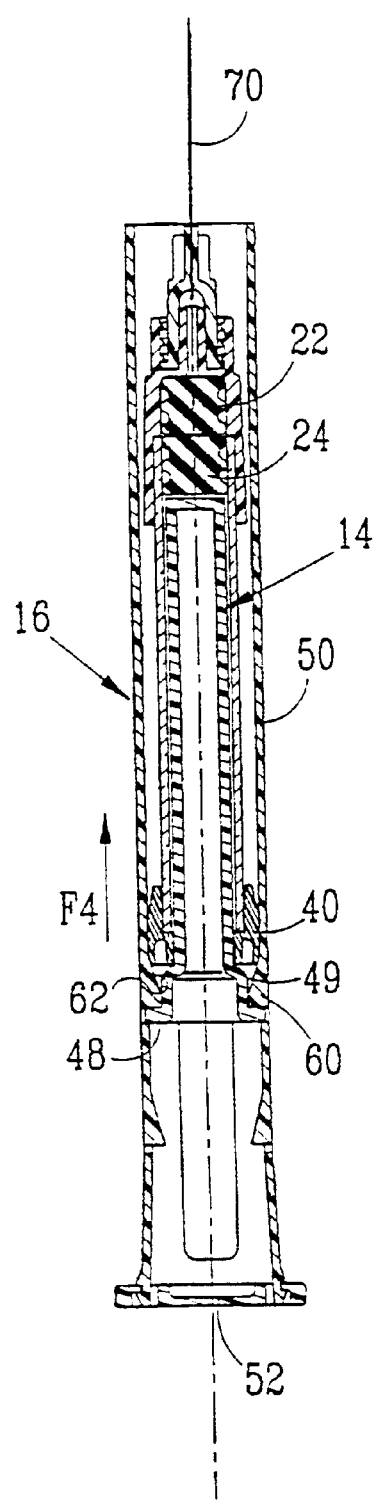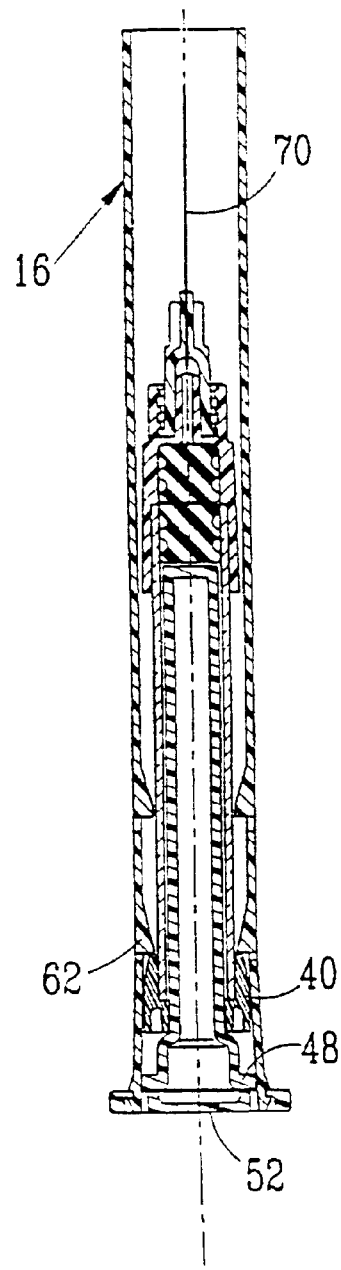
FIG.4
FIG.5

INJECTION SYRINGE WITH EXTERNALLY MOBILE NEEDLE SHIELD

BACKGROUND OF THE INVENTION

The present invention relates to an injection syringe of the type comprising, on the one hand, an elongate syringe body comprising a tube and a perforated front wall capable of receiving an injection needle and, on the other hand, a rear actuating plunger mounted so that it can move inside the tube, which syringe further comprises a mobile needle shield that can move externally along the syringe body between a retracted position drawn back from the injection end of the needle and an active protecting position in which the front end of the shield is forward of the injection end of said needle, there also being means of axial coupling between the shield and the actuating plunger to cause them to move simultaneously forward along a common portion.

A syringe of the aforementioned type is described, for example, in international patent application WO-97/02855 filed in the name of the applicant company.

In the syringe described in that document, the needle protector or shield consists of a tube that can be moved externally along the syringe body. The tube is fixed permanently to the rear end of the actuating plunger. This end is equipped with a disk on which a finger can press when the syringe is actuated.

Thus, the actuating plunger and the needle shield can be moved simultaneously and cover travels of the same length.

The minimum travel of the needle shield has a length equal to the sum of the lengths corresponding, on the one hand, to the length of the syringe body filled with liquid for injection and, on the other hand, to the length of the needle projecting from the body, to which is added a travel that prevents a finger from touching the end of the needle.

In order to allow the needle shield to move beyond the end of the needle, it is appropriate that after injection, the piston should be free to slide in the syringe body over a length roughly equal to the length of the portion of the needle that projects from the syringe body.

Thus, the syringe body has to be very long, even though only the rear part of the body is actually intended to contain the liquid for injection.

In addition, in order to withdraw liquid, it is necessary for the needle to project into the syringe body. Thus, the needle cannot be interchangeable.

SUMMARY OF THE INVENTION

An object of the invention is to provide an injection syringe that makes it possible to reduce the length of the syringe body, thus making the use of standard and interchangeable needles possible.

To this end, a subject of the invention is an injection syringe of the aforementioned type, characterized in that it comprises means of releasing the coupling means to disconnect the actuating plunger and the needle shield during the final phase of the fitting of the needle shield.

According to some particular embodiments, the injection syringe has one or more of the following features:

said release means can be actuated under the control of the needle shield sliding along the syringe body;

it comprises a strong pointer identifying an intermediate position of the shield as it slides along the syringe body, in which position the needle shield is immediately upstream of the release means;

the means of axial coupling comprise means of elastically engaging the needle shield with the actuating plunger (14) and the release means are designed to disengage said means of elastic engagement;

the release means comprise a cam/follower arrangement carried by the needle shield and the syringe body, which arrangement is designed to cause the elastic deformation of the needle shield with a view to disengaging the means of elastic engagement as the needle shield moves;

the needle shield has an operating zone designed to cause the simultaneous movement of the shield and of the actuating plunger along said common portion, which common portion corresponds to the travel of the actuating plunger at the time of injection; and the coupling means are designed to axially secure the needle shield and the actuating plunger together in both directions over said common portion.

BRIEF DESCRIPTION OF THE DRAWINGS

The invention will be better understood with the aid of the description which will follow, which is given solely by way of example and made with reference to the drawings in which:

FIG. 4 is a view in longitudinal section of the same syringe depicted after injection and after the needle has been removed from the body of the patient; and FIG. 5 is a view in longitudinal section of the syringe after the needle shield has been fitted.

DETAILED DESCRIPTION OF THE INVENTION

Figure 1:
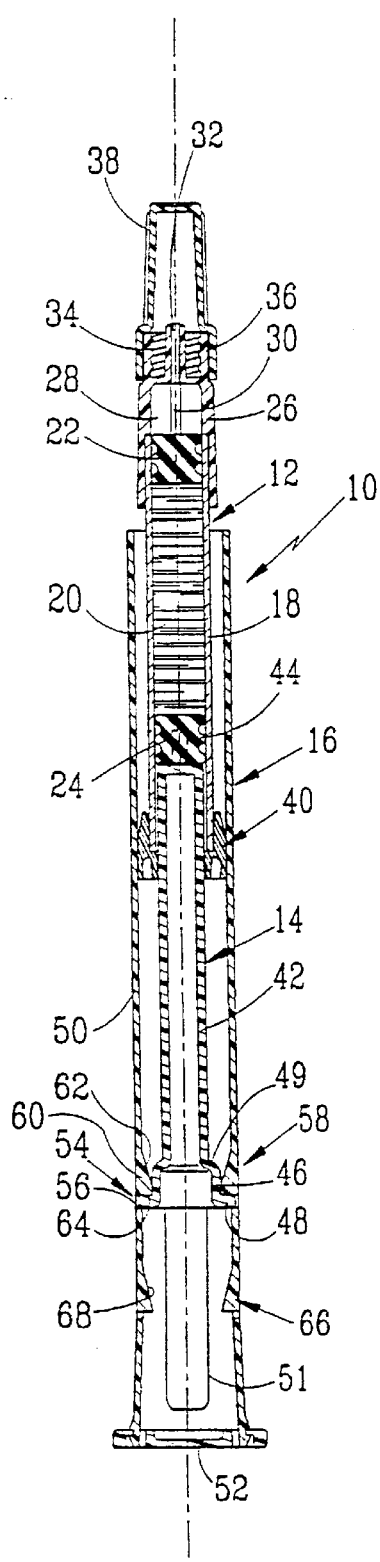
FIG. 1 is a view in longitudinal section of a syringe according to the invention, prior to use.

The injection syringe 10 depicted in FIG. 1 has an overall shape with symmetry of revolution about an axis X—X. This syringe is a use-once syringe. It is supplied ready to use, already containing a medical fluid for injection.

The syringe essentially comprises an elongate syringe body 12, a rear actuating plunger 14 mounted so that it can move inside the body 12 and a needle shield 16 mounted so that it can move by sliding on the outside of the syringe body.

The syringe body 12 comprises a cylindrical glass tube 18, open at both ends. The liquid for injection, denoted 20, is held inside the glass tube 18 between a front piston 22 and a rear position 24. These pistons are made of elastomer.

At the front, the glass tube 18 is extended by a needle support 26 forming the front wall of the syringe body. The front end of the tube 18 is push-fitted into the needle support 26.

Forward of the glass tube 18, the needle support 26 delimits a chamber 28 for housing the front piston 22. This chamber extends the duct delimited by the glass tube 18. It has a length slightly greater than that of the front piston 22. In addition, it has a diameter slightly smaller than that of the front piston 22, to ensure that the latter is wedged firmly in place.

Formed on the wall of the chamber 28 is a longitudinal canal 30 opening at a first end inside the glass tube 18 and at its other end into an injection passage 32. The latter is formed axially in an external lump 34 intended to receive the injection needle.

The external surface of the lump 34 is approximately frustoconical and defines a Luer hub of suitable dimensions to receive standard injection needles. The lump 34 is surrounded by an integrally-formed skirt 36. On the inside, this skirt has a screw thread intended to collaborate with tabs provided on the mounting fitting of standard needles.

A cap 38 is pushed onto the skirt 36 to protect the attachment end of the needle.

At its rear end, the glass tube 18 carries a pushed-on and bonded finger support ring 40. This finger support ring forms an annular protrusion around the tube 18. It also comprises two radially projecting lugs. These form supports for two fingers of the hand during injection.

The actuating plunger 14 comprises, on the one hand, the rear piston 24 and, on the other hand, a rigid push rod 42, the front end of which is engaged inside the syringe body 12. This front end is equipped with a threaded lump 44 received in a corresponding recess of the rear piston 24, so as to secure these axially together in both directions.

The plunger push rod 42 has a tubular overall shape. At its rear end it has a flared portion 46. This portion is bordered at its free end by radial fingers 48 distributed at the periphery of the piston rod. The flared portion defines, with the main part of the rod 42, a shoulder 49.

The needle shield 16 is generally in the form of a tube or sleeve 50. It is made of an elastically deformable semi-rigid material. Along a part of its length it has two diametrically opposed longitudinal slots 51 designed for the passage of the lugs of the finger support ring 40.

Moreover, at its rear end, the needle shield 16 has a disk or roundel 52 for the thumb to rest against during injection. This roundel is connected by snap-fastening to the rear end of the tube 50.

Along its length, the shield 16 has means 54 for coupling the plunger 14 and the shield 16 in terms of translation. These means 54 secure these parts together in both directions. They comprise a ring of radial apertures 56 passing through the wall of the tube 50. Engaged in these apertures are the radial fingers 48 provided at the rear end of the plunger push rod 42.

Thus, coupling is provided by elastic engagement of the fingers 48 in the apertures 56.

The front and rear edges delimiting the apertures 56 collaborate with the fingers 48 to secure the piston and the shield together respectively at the rear and at the front.

Forward of the apertures 56, when considering the direction in which the plunger 14 is pushed into the body 12, there are means 58 for releasing the coupling between the plunger 14 and the shield 16.

In the embodiment depicted, the release means 58 comprise internal projections 60 delimiting ramps 62 designed to collaborate with the finger support ring 40, so as to locally deform the tube 50 in the region of the radial apertures 56. The projections 60 have a thickness that increases progressively toward the rear of the syringe and which ends in straight-cut faces 64 bordering the apertures 56. The ramps 62 thus converge toward the axis of the syringe in the direction of the rear of the syringe. They constitute cam surfaces designed to collaborate with the periphery of the finger support ring 40 which constitutes a cam-follower; the ramps 62 and the support ring 40 together form a cam-and-follower arrangement.

Advantageously, the distance separating the coupling means 54 from the disk 52 is very slightly greater than the total length of the longest standard needle that can be mounted on the syringe. In practice, this length is very slightly greater than 1" (2.54 cm) and for example is 2.6 cm.

Between the coupling means 54 and the disk 52 there are snap-fastening means 66 designed to lock the needle shield in its active protecting position in which the front end of the shield is forward of the injection end of the needle.

The snap-fastening means 66 comprise elastically deformable tabs projecting toward the inside of the tube 50. These tabs delimit ramps 68, the normal to which is oriented toward the front of the syringe.

The ramps 68 are designed to collaborate with the periphery of the finger support 40, forming a cam surface which causes them to deform elastically as they pass the finger support ring 40 during the movement of the shield 16.

To the rear of the snap-fastening means 66, the internal surface of the shield 16 is frustoconical and flares out toward the disk 52. Immediately before the disk 52, the inside diameter of the shield is equal to the outside diameter of the plunger push rod 42 at its end carrying the fingers 48.

The syringe depicted in FIG. 1 is assembled as follows.

First of all, the glass tube 18 is filled with the liquid 20 for injection, which is contained therein between the two pistons 22 and 24. The front end of the glass tube 18 is then fitted with the needle carrier 26 and the protective cap 38. Once the finger support ring has been fitted at the rear end of the glass tube 18, the plunger push rod 42 is screwed into the rear piston 24. The protective tube 50 equipped with the disk 52 is finally fitted around the syringe body. It is mounted around the finger support ring 40 by elastic deformation.

Likewise, during assembly, the fingers 48 penetrate the apertures 56 by elastic deformation of the tube 50 as the fingers 48 pass the projections 60.

Figure 2:
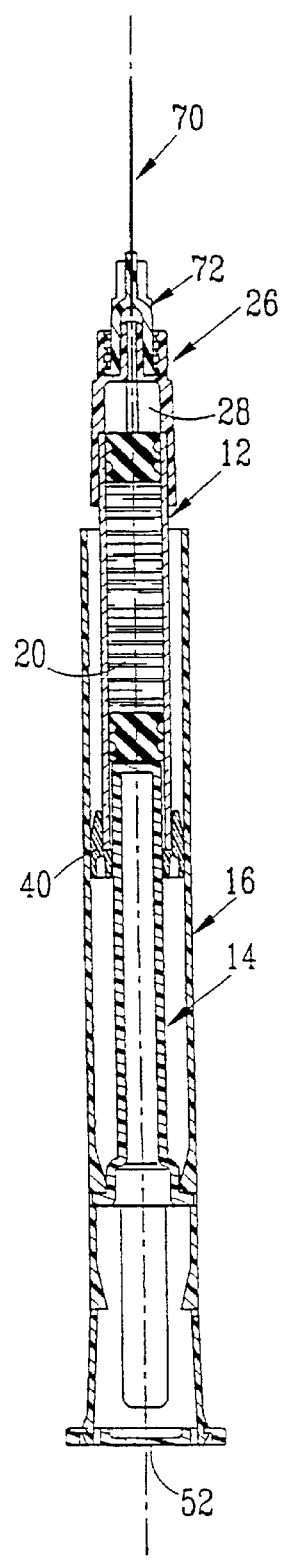
FIG. 2 is a view in longitudinal section of the syringe of FIG. 1, depicted fitted with a needle.

In order to use the syringe depicted in FIG. 1, the practitioner first of all removes the protective cap 38 and equips the needle holder 26 with an injection needle 70 equipped with a Luer hub fitting 72, as depicted in FIG. 2.

The plunger 14 is then gradually pushed into the syringe body, by pressing on the disk 52. The pushing in of the actuating plunger 14 causes the simultaneous movement in the syringe body of the pistons 22 and 24 and of the liquid 20 for injection.

Figure 3:
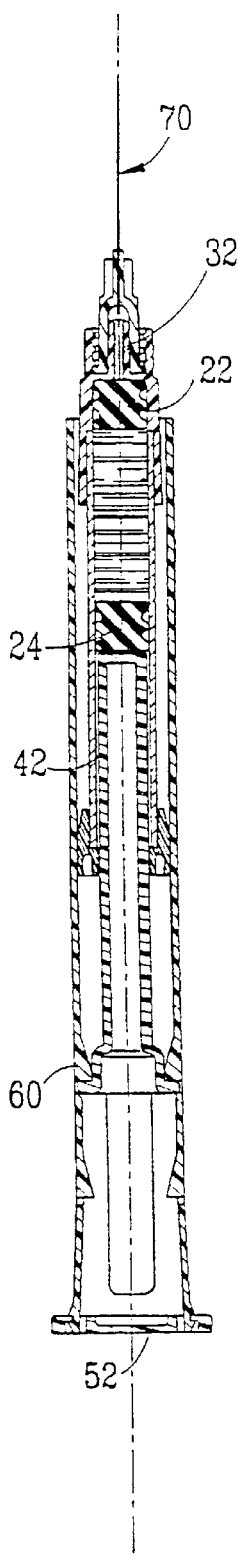
FIG. 3 is a view in longitudinal section of the same syringe ready to inject.

The front piston 22 then enters the chamber 28 as depicted in FIG. 3. As the length of the chamber 28 is slightly greater than that of the piston 22, the liquid 20 is free to flow through the longitudinal canals 30.

When the actuating plunger 14 is later pushed into the syringe body, since the front piston 22 is immobilized, the liquid for injection flows through the canals 30 to reach the injection needle 70.

If the liquid 20 contained in the syringe body is designed to be injected by itself, the practitioner then carries out injection in the conventional way. When the rear piston 24 comes into contact with the front piston 22, all the liquid 20 contained between them has been discharged through the injection needle 70.

If, on the other hand, the liquid 20 initially contained in the syringe has to be combined, during extemporaneous mixing, with an active substance contained in an intermediate container, the liquid 20 is injected into the container by depressing the plunger 14.

When the rear piston 24 comes into contact with the front piston 22, opposition to the subsequent movement of the needle shield 16 is encountered by the practitioner. This opposition constitutes a pointer indicating that, for subsequent depression of the shield, the piston will become detached.

The opposition is formed by the projections 60 coming into contact with the finger support ring 40 simultaneously with contact between the two pistons 22 and 24. The force needed to overcome this opposition corresponds to the force needed to deform the shield under the action of the ramps 62 collaborating with the finger support ring 40.

Under these conditions, it is possible for the practitioner to completely empty the syringe without fitting the needle shield and thus to re-use the syringe to inject the preparation.

In order to draw up the injectable preparation obtained by the mixing of the active substance and of the liquid 20, the practitioner extracts the plunger 14 from the syringe body by pulling on the rear end of the tube 50. Under the action of the depression formed between the front pistons 22 and 24, the preparation is drawn back up inside the syringe body 12.

As the diameter of the chamber 28 is slightly smaller than the diameter of the piston 22, the latter remains jammed in the chamber 28 when the injectable preparation is being drawn up.

Injection is then carried out as described earlier.

At the end of injection, whether or not this has been preceded by a phase of extemporaneous mixing of substances for injection, the syringe is in the position depicted in FIG. 4.

By continuing to apply force to the disk 52, the practitioner causes local deformation of the tube 50 in the region of the means 54 for coupling the plunger 14 and the needle shield.

What happens is that the ramps 62 engage around the finger support ring 40. As the shield 16 moves in the direction of the arrow F4 of the tube 50, the plunger push rod 14 is immobilized with respect to the syringe body, on the one hand, by the fact that the rear piston 24 is resting against the front piston 22 and, on the other hand, by the shoulder 49 resting against the finger support ring 40.

Under the action of the deformation of the tube 50, the radial apertures 56 move away from the fingers 48, which therefore find themselves disengaged from the apertures.

Thus, the coupling between the actuating plunger 14 and the needle shield 16 is released and the external sliding of the needle shield 16 continues along the syringe body 12 while the plunger 14 is immobile within the syringe body.

The needle shield continues to move until the front end thereof is forward of the injection end of the needle, as depicted in FIG. 5.

In this position, the snap-fastening tabs 66 bend down in front of the finger support ring 40, thus locking the needle shield 16 in its active protecting position, therefore preventing it from returning as a result of tension exerted on the tube 50.

In the position depicted in FIG. 5, the fingers 48 provided at the rear end of the plunger push rod 42 are immediately forward of the disk 52, where the inside diameter of the shield is designed to receive the latter.

The detachment of the plunger from the shield at the end of injection, during the final phase of fitting the needle shield, makes it possible to reduce the length of the syringe body. Thus, the syringe body can be equipped with a standard needle that can be attached using a Luer hub, because there is no need for the needle to extend up inside the syringe body.

What is claimed is:

1. An injection syringe (10) comprising:

an elongate syringe body (12) comprising a tube (18) and a perforated front wall (26) capable of receiving an injection needle (70);

a rear actuating plunger (14) mounted so that it can move inside the tube (18),;

a mobile needle shield (16) that can move externally along the syringe body (12) between a retracted position, drawn back from an injection end of the needle (70), and an active protecting position in which a front end of the shield (16) is forward of the injection end of said needle (70);

a means for coupling (54) for axially interconnecting the shield (16) and the actuating plunger (14) to cause them to move simultaneously forward along a common portion; and a means for releasing (58) for releasing the means for coupling (54) to disconnect the actuating plunger (14) and the needle shield (16) during a final phase of fitting of the needle shield (16).

2. The injection syringe according to claim 1, characterized in that said means for releasing (58) can be actuated under control of the needle shield (16) sliding along the syringe body (12).

3. The injection syringe according to claim 2, comprising a strong pointer (60) identifying an intermediate position of the shield (16) as the needle shield slides along the syringe body (12), in which position the needle shield (16) is immediately upstream of the means for releasing (58).

4. The injection syringe according to claim 3, characterized in that the means for coupling comprises means for elastically engaging the needle shield (16) with the actuating plunger (14), and the means for releasing (58) is designed to disengage said means for elastically engaging the needle shield.

5. The injection syringe according to claim 4, characterized in that the means for releasing comprises a cam-and-follower arrangement carried by the needle shield (16) and the syringe body (12), which arrangement is designed to cause elastic deformation of the needle shield (16) with a view to disengaging the means for elastically engaging as the needle shield (16) moves.

6. The injection syringe according to claim 1, characterized in that the needle shield (16) has an operating zone (52) designed to cause simultaneous movement of the shield (16) and of the actuating plunger (14) along said common portion, which common portion corresponds to a travel of the actuating plunger (14) at a time of injection.

7. The injection syringe according to claim 1, characterized in that the means for coupling is designed to axially secure the needle shield (16) and the actuating plunger (14) together in both directions over said common portion.

8. (Amended) The injection syringe according to claim 2, characterized in that the means for coupling comprises means for elastically engaging the needle shield (16) with the actuating plunger (14), and the means for releasing (58) is designed to disengage said means (54) for elastically engaging the needle shield, and in that the means for releasing (58) comprises a cam-and-follower arrangement carried by the needle shield (16) and the syringe body (12), which arrangement is designed to cause elastic deformation of the needle shield (16) with a view to disengaging the means for elastically engaging the needle shield as the needle shield (16) moves.

* * * * *